United States Patent [19]
Dooner et al.

[11] Patent Number: 5,013,658
[45] Date of Patent: May 7, 1991

[54] TRANSPOSON TAGGING OF GENES IN TRANSFORMED PLANTS

[75] Inventors: Hugo Dooner, Walnut Creek; Jonathan Jones, Alameda; Pal Maliga, Moraga, all of Calif.

[73] Assignee: DNA Plant Technology Corporation, Mt. Kisco, N.Y.

[21] Appl. No.: 193,966

[22] Filed: May 13, 1988

[51] Int. Cl.$^5$ .................. C12N 15/00; C12N 1/20; C12N 1/00; C12N 5/00
[52] U.S. Cl. .................. 435/172.3; 435/172.1; 435/240.4; 435/252.2; 435/252.3; 435/317.1; 435/320.1; 435/91; 935/1; 935/30; 935/67; 935/73; 800/205; 47/DIG. 1
[58] Field of Search ............... 435/172.1, 172.3, 252.3, 435/252.2, 320, 317.1, 240.4; 935/1, 67

[56] References Cited

U.S. PATENT DOCUMENTS 4,732,856 5/1988 Federoff ..................... 435/172.3

OTHER PUBLICATIONS

Benzion et al., 1986 in Internal Cong Plant Tissues and Cell Culture, Somers (ed.) p. 131.
Hain et al., 1985 Mol. Gen. Genet. 199:161–168.
Garfinkel et al., 1981 Cell 27:143–153.
Andre et al. 1986 Mol. Gen. Genet. 204:512–518.
Velten et al., 1984, *Embo J.*, 3:2723–2730.
Sanders et al., 1987 (Feb.) Nucl. Acids Res 15:1543–1558.
Maliga, 1984, Annu. Rev. Pl. Physiol 35:530–532.
Jones et al., 1987 (Nov.) Mol. Gen Genetics 210:86–91.
van den Elzen et al., 1985, Plant Molic Biol. 5:299–302.
Nevers, P., et al., *Adv. Bot. Res.*, 12:103–203 (1986).
McClintock, B., *Cold Spring Harbor Symp. Quant. Biol.*, 21:197–216 (1956).
McClintock, B., *Carnegie Inst. Wash. Yrbook*, 53:254–260 (1954).
Robertson, D. S., *Mutat. Res.*, 51:21–28 (1978).
Baker et al., *Pnas USA*, 83:4844–4848 (1986).
Van Sluys et al., *Embo J.*, 6:3881–3889 (1987).
Federoff, N. et al., *Pnas USA*, 81:3825–3829 (1984).
Paz-Ares, J. et al., *Embo J.*, 5:829–833 (1986).
Martin et al., *Embo J.*, 4:1625–1630 (1985).
Baker, B. et al., *Embo J.*, 6:1547–1554 (1987).
Jones, J. D. et al., "A Visual Assay for AC Transposition in Dicots", Abst. Y 221, *J. of Cellular Biochem.*, Suppl. 12C, 1988, p. 267.

*Primary Examiner*—Elizabeth C. Weimar
*Assistant Examiner*—P. Rhodes
*Attorney, Agent, or Firm*—Townsend and Townsend

[57] ABSTRACT

This invention relates to improved methods for transposon tagging as a route to plant gene isolation. The specific improvements comprise efficient means for preselecting plants which have undergone transposition. Through use of this preselection, it is possible to substantially reduce the number of plants which must be inspected to locate individuals having the transposon excised and inserted into a gene of interest. The result is a substantial savings in time, costs and efficiency associated with growing and screening large numbers of plants for tagging and isolation of a desired plant gene.

17 Claims, 2 Drawing Sheets

TRANSPOSON TAGGING OF GENES IN TRANSFORMED PLANTS

BACKGROUND OF THE INVENTION

1. Field of the Invention

This invention relates to improved methods for transposon tagging and plant gene isolation. The specific improvements comprise efficient means for preselecting plants that have undergone transposition. Through use of this preselection, it is possible to substantially reduce the number of plants which must be inspected to locate individuals having the transposon excised and inserted into a gene of interest. The result is a substantial savings in time, costs and efficiency associated with growing and screening large numbers of plants for tagging and isolation of a desired plant gene.

Plants contain many genes having potential use for crop improvement. A limiting factor is the means to isolate useful genes. Many genes of interest, for instance genes encoding disease resistance, are difficult or impossible to isolate using standard biochemical or genetic engineering techniques.

One approach to gene isolation in plants has involved the use of transposable elements. A transposable element (TE) is a type of DNA sequence which has the ability to move or "jump" to new locations in the genome. A TE can insert into existing genes and by so doing cause mutation by gene disruption. TEs are known in bacteria, Drosophila, yeast, nematodes, plants and mammals and are believed to be ubiquitous.

A major limitation to transposon tagging as a means to isolate genes in plants is the fact that transposition in plants is a low frequency event. Typically, on the order of 1% of seed progeny may show evidence of transposition. Moreover, the chances of a TE landing in a particular gene of interest (for purposes of transposon tagging) is low because of the large number of DNA sequences into which transposition could take place. The overall frequency of detection of mutation due to TE insertion in a gene of interest is typically less than one in 10,000 (as a proportion of progeny seed screened). This means that well in excess of 10,000, and perhaps in the order of 100,000, plants may need to be screened for a high probability of identifying such a mutation.

2. Information Disclosure

Plant transposons are known. Transposon systems have been reported in Antirhinum majus, petunia and soybean. Nevers, P., et al., Ann Bot. Res., 12: 103-203, (1986). Corn is one of the better studied systems with several families of transposable elements having been investigated. Three families have received the most attention: the Ac/Ds system (McClintock, B., Cold Spring Harbor Symp. Quant. Biol., 21:197-216, 1956); the Spm/En system (McClintock, B., Carnegie Inst. Wash. Yrbook, 53:254-260, 1954); and the Mu system (Robertson, D.S., Mutat. Res., 51:21-28, 1978).

There have been reports that TEs, including Ac, can function (i.e., transpose) in plant species other than the one from which they originated. Baker, et al., PNAS USA 83: 4844-4848 (1986) and Van Sluys et al., EMBO J., 6:3881-3889 (1987).

The corn transposons Ac/Ds and Spm have been used for gene isolation in corn. Federoff, N., et al., 30 PNAS USA, 81:3825-3829 (1984) and Paz-Ares, J., et al., EMBO J., 5, 829-833(1986). Transposons have also been used to isolate genes from Antirhinum majus. Martin et al., EMBO J 4:1625-1630 (1985).

An assay permitting the selection in tissue culture for Ac transposition events has been reported Baker, B., et al., EMBO J 6:1547-1554, (1987). This assay involved placing the Ac DNA in the 5' untranslated region of a chimeric kanamycin resistance gene in a way which meant that the drug resistance gene was inoperative until Ac excision took place. Thus, they could select for Ac excision by placing transformed calli on kanamycin.

SUMMARY OF THE INVENTION

This invention relates to a method for isolating a plant gene of interest conferring a characteristic phenotype, wherein said method comprises: (a) transforming a plant carrying the gene of interest to make transformed plants by introduction of a DNA construct containing a transposon inserted within a selectable marker rendering that marker inoperable; and (b) isolating those transformed plants having the transposon excised from the marker and inserted into the plant gene of interest. Preferred selectable markers include those that confer or effect resistance to an antibiotic upon a plant cell and selectable markers that permit identification by the presence or absence of chlorophyll in the plant cells in which the markers are operational and functioning. An especially preferred selectable marker effects resistance to streptomycin such as a gene encoding streptomycin phosphotransferase, e.g., the selectable marker derived from the gene encoding streptomycin phosphotransferase contained in the bacterial transposon Tn5.

For controlling the selectable markers of this invention, especially the streptomycin phosphotransferase, it is preferred that the marker is operably linked to a promoter selected from the group consisting of the 2' promoter from Agrobacterium tumefaciens and the 35s promoter from cauliflower mosaic virus.

Preferred transposons include those selected from the group of transposable elements comprising: Ac; Spm; and Tam 3.

The preferred plant cells for this invention are dicotyledenous plants and especially preferred are species of Nicotiana.

The preferred plant genes for location using this invention are those which have an effect on resistance to disease, or on biochemical composition of seed (e.g., starch, lipid, protein or secondary plant product composition).

More specifically this invention involves a method which comprises recombining a transposon into a selectable marker rendering the marker inoperable; transforming a plant cell with another marker linked to the inoperable marker; maintaining the transformed cells under conditions suitable for the transposon to transpose from the marker to the plant gene; and isolating those cells having the transposon recombined into the plant gene. This method is more specifically described by the following steps: (a) selecting a plant containing the plant gene of interest; (b) preparing a DNA construct comprising a plant promoter operably fused to a DNA segment coding for streptomycin phosphotransferase and further comprising the transposon Ac wherein the transposon is positioned within the DNA segment so as to render the streptomycin phosphotransferase gene incapable of conferring resistance to streptomycin in the plant hosting the construct; (c) introducing said DNA construct into the plant by transformation to yield a multiplicity of transformed plants and identifying plants in which said introduced DNA construct is genetically linked to the target gene; (d) growing the transformed plants in the presence of streptomycin and selecting from the plants a set of plants which exhibit excision in which the Ac DNA has excised from the streptomycin phosphotransferase gene, said plants which exhibit excision being identifiable by streptomycin resistance; (e) selecting from the plants which exhibit excision, a plant in which the desired phenotype, i.e., the phenotype corresponding to the gene of interest, is altered (e.g., reduced, enhanced or eliminated) as the result of transposition of the Ac DNA into the plant gene encoding the desired phenotype; (f) creating a genomic library from the DNA of the plant of step e; (g) isolating from said genomic library a clone containing transposon Ac DNA using labeled transposon Ac DNA as a probe; and (h) isolating the gene of interest from a library derived from a plant containing the gene of interest by using a probe DNA linked to transposon Ac in said clone containing transposon Ac DNA.

In addition to the above described methods, this invention provides for DNA constructs comprising a DNA segment containing at least one selectable marker for use in plant cells that is operably linked to a plant promoter and further comprising a transposon positioned within the segment, said transposon rendering the marker inoperable until the transposon removes itself. The preferred selectable markers are as described above for the methods of this invention. The constructs preferably comprise a second selectable marker operable in a plant cell such as a marker that encodes for resistance to kanamycin. These constructs are typically capable of being stably maintained by *Agrobacterium tumefaciens* which is the preferred transformation system.

Host cells containing the above constructs as either extrachromosomal entities or as incorporated chromosomal recombinations (insertions) are a part of this invention.

DETAILED DESCRIPTION

This invention relates to an improved method of isolating plant genes. In accordance with the invention, novel methods and novel constructs are provided for use in transposon tagging and plant gene identification.

More particularly, the method of the invention involves the preparation and use of novel DNA constructs comprising a transposon, the transposon being recombined within a DNA segment encoding for a selectable marker. The construct is introduced into a plant by transformation. The transformants are then pre-screened for transposition based on the presence of the marker.

Those transformants having the phenotype effected by the selectable marker are further selected for a change in the phenotype being conferred by the gene of interest. These individuals are isolated and their genomic DNA isolated and probed for the presence of the transposon. The detection of the transposon permits the isolation of the gene of interest.

Transposable elements (TE) for use in this invention are well known in the art. Many plants are known to contain TEs. They are typically detected by variegation arising from somatic mutation A review of the known TEs can be found in Nevers et al., Adv. in Bot Res. 12:103–203 (1987), which is incorporated herein by reference. Any of the known autonomous (i.e., self-mobilizing) plant TEs or a combination of autonomous and non-autonomous plant TEs can be used in the invention described herein. However it is preferred that the TE preferentially transpose to closely linked sites and effect rates of germinal transposition in excess of about 1%. Preferred TEs include the Spm/En system from corn and the Tam 3 system from Antirhinum majus, and most preferred is Ac/Ds from corn.

Various ways are known to isolate novel TEs from plant sources. For instance, one could choose a genetic locus which encodes a known protein product and which is also known from genetic data to contain a transposable element in a given mutant line. With the help of antibodies against the gene products of the locus and appropriate cDNA probes, the genomic sequence of the locus can be cloned from wild-type plants. This in turn is used to isolate the corresponding sequence from the mutant. Nevers, P., et al., supra.

The DNA construct for transforming the plant cell contains a selectable marker into which the TE is inserted. The marker is preferably readily detectable when functioning and genomically incorporated. Selectable markers of use in this invention include antibiotic resistance, e.g., resistance to kanamycin, hygromycin, methotrexate, bleomycin, chlorsulfuron, phosphinotricine or glyphosate (resistance to all of which has been introduced into plants by transformation). Plant sensitivity to the above antibiotics results in death. More preferred are those markers for resistance to antibiotics which permit nonlethal differentiation between sensitive and resistant plants. Non-lethal markers include gentamycin, lincomycin, clindamycin and spectinomycin. Most preferred is streptomycin resistance, in particular the streptomycin phosphotransferase marker described herein.

Plant cells, e.g., tobacco (*Nicotiana tabacum*), Arabidopsis, Brassica and lettuce, respond to streptomycin by bleaching. This bleaching is generally lethal in plants since photosynthesis cannot be carried out in the absence of photosynthetic pigments. When sucrose, or other suitable carbon source is made available, bleaching is not lethal, since survival is not dependent on photosynthesis. Spontaneous mutants of tobacco have been isolated that are able to green on the selective medium containing streptomycin. Maliga, P. et 5 al , Nature, 255:401–402 (1975); and Fluhr, R. et al., PNAS USA, 8:1485–1489 (1985). However the appearance of such mutations is rare in cell culture or in plants. Maliga, P., Ann. Rev. Plant Physiol , 35:519–542 (1984).

Selection for streptomycin resistance has been carried out in seedlings or in cell culture.

Streptomycin resistance has also been engineered in plants as a dominant genetic marker by expressing a streptomycin phosphotransferase from Tn5 (Jones, J., et al., 1987, Mol. Gen Genet. 210:86-91, which is incorporated herein by reference).

Resistance to streptomycin may be based on mutations in the 16S rRNA genes (Montandon, P. E., et al., Nucl. Acids Res., 13:4299-4310, 1985) or on mutations in ribosomal protein genes (Funatsu, G. et al., J. Mol. Biol., 68:547-550, 1972). A common form of plasmid-determined streptomycin resistance in bacteria is based on enzymatic conversion of the drug into inactive form. The conversion may involve phosphorylation or adenylation (Davies, J., et al., Ann. Rev. Microbiol., 32:469-518, 1978). One of the converting enzymes well studied is streptomycin phosphotransferase (SPT) carried by the bacterial transposon Tn5 (Mazodier, P., et al., Mol. Gen. Genet., 192:155-162, 1983; and Putnoky, P., et al., Mol. Gen. Genet., 191:288-294, 1983).

The SPT gene is a preferred selectable marker for use in this invention. The sequence of the internal portion of Tn5 has been determined, and the probable translational initiation site of the SPT gene established (Mazodier, P., et al., Nucleic Acids Res., 13:195-203, 1985). Tn5 confers streptomycin resistance on bacteria, such as *Agrobacterium tumefaciens*, but not *Escherichia coli*. Mazodier, P., et al., (Mol. Gen. Genet. 204:404-409, 1986) showed that mutant forms of the SPT gene could be isolated which, unlike the wild type, did confer streptomycin resistance on *E. coli*. Analysis of these forms showed that they contained a 2 amino acid deletion near the carboxy-terminus of the protein. It is this allele which is particularly preferred.

The DNA construct must be capable of transformation into a host plant cell. Typically, the construct involves the use of the Agrobacterium based transformation system in which transferred DNA (T-DNA) is defined by left and right border sequences in a binary vector. This DNA is transferred from Agrobacterium strains to the plant cell and integrates at random locations in the plant chromosome. Thus, such T-DNA does not need an independent replication origin since it replicates along with the adjacent plant DNA into which it integrated. Suitable bacterial selectable markers for bacterial cells include ampicillin, tetracycline, and gentamycin resistance. Suitable selectable markers for plant cells are detailed above. The origins of replication for bacterial cells include ColEI and RK2.

The class of plant selectable markers is limited only in that the marker needs to be capable of functioning after the TE has excised. Thus, the particular promoter region and polyadenylation sequence are variable elements of the construct. The promoter is preferably constitutive or readily controllable and thus the promoter can be either the native promoter or a chimeric promoter. For example the cauliflower mosaic virus 35S promoter, nopaline synthase promoter and mannopine synthase (2') promoter are amenable for use in controlling the plant selectable markers useful in this invention. In combination with the preferred selectable marker of this invention, the 2' promoter from the Ti plasmid Ach 5 is preferred.

The specifics of the recombinations necessary to create a DNA construct suitable for use in this invention need not be provided in any detail. Using standard techniques commonly used in genetic recombinations such as those taught in Maniatis et al., 1985, Molecular Cloning. A Laboratory Manual, Cold Spring Harbor Lab. Press, NY, it is possible to construct an unlimited number of recombinant DNA constructs capable of duplicating the method for plant gene isolation described herein.

The location and method of insertion of the TE sequence can vary as long as the insertion prohibits the selectable marker from operating and its excision permits phenotypic expression of the marker. Preferably the TE is inserted in the 5' untranslated region of the marker. Often times unique restriction sites are preferably introduced in order to create a DNA construct for use in the disclosed invention. Methods for introducing such sites are well known in the art.

Cell culturing techniques for plant cells are well known with many review articles available to teach the specific requirements for each plant species, e.g., Vasil, I. K., Cell Culture and Somatic Cell Genetics of Plants, Vol 1. Academic Press, Inc. NY, 1984; and Evans, D., et al., Handbook of Plant Cell Culture, Vol. 1, MacMillan Publishing Co., 1983.

The techniques for introducing recombinant DNA into plant cells are also well known and include the use of *Agrobacterium tumefaciens* in concert with the binary vector T-DNA borders (Van den Elzen, P., et al., Plant Mol. Biol., 5:149-154, 1985), direct DNA transfer induced by chemical treatment with polyethylene glycol (Krens, F. A., et al., Nature 296:72-74, 1982; Paszkowsi, J., et al., EMBO J. 3:2717-2722, 1984), electroporation (Fromm et al., Nature 319:791-793, 1986), microinjection CrossWay, Mol. Gen. Genet. 202:179-185, 1985) and microprojectiles coated with DNA (Klein, T. M., et al., Nature, 327, 70-73, 1987).

The method of this invention permits one to isolate a plant gene of interest. The plant containing the gene of interest may be any type of plant, higher or lower, dicot or monocot, which is amenable to transformation. The gene of interest can be any gene having an identifiable phenotype, e.g., genes encoding disease resistance, genes for specific biochemical pathways such as pigment biosynthesis or fatty acid biosynthesis, cytoplasmic male sterility restorer genes, hormone biosynthetic genes, hormone response genes or developmental genes.

By an identifiable phenotype, it is meant that the action of the gene of interest is sufficiently understood that the change in the phenotype due to an insertion by a TE can be recognized. That is, once the transformed cells are isolated, a determination of the presence or absence of the mutant phenotype of interest due to the TE needs to be made. Typically the gene of interest will be available in a dominant homozygous form. Cells from these dominant homozygotes are used for transformation with the transposon constructs described above. It is preferred that the transposon construct and the gene to be targeted are genetically linked. This is achieved by making many independent transformed plant lines and mapping the T-DNA inserts with respect to their position relative to the target gene. Preferably transformants in which an active introduced transposon is linked to the target gene are used in the transposon mutagenesis experiment. Such individuals are then crossed to individuals which contain a recessive mutation or which otherwise lack the dominant function expressed by the targeted gene.

More specifically, progeny individuals are subjected to two forms of analysis. Firstly, they are prescreened for individuals in which Ac excision from the target gene had taken place by selection for drug resistance. For instance, from 100,000 progeny, perhaps 2000 such individuals are selected. Secondly, these individuals would be inspected for the whole plant phenotype of interest. Individuals which exhibit the phenotype corresponding to a loss or alteration of function of the gene of interest are selected (for subsequent inspection) as having the transposon in one of the mutant alleles. At this point, orthodox gene cloning procedures can be used to first isolate the transposon tagged mutant DNA sequences and then isolate wild type gene sequences from a wild type library made from DNA of a plant carrying the dominant allele of the gene.

Even more specifically, the disclosed invention involves the preparation and use of novel constructs containing a plant promoter and an Ac transposon, the transposon being within DNA encoding streptomycin resistance. The construct is introduced into a plant by transformation to yield a multiplicity of transformed plants (transformants).

It is particularly convenient but not necessary to have a first selectable marker to identify those cells that have been transformed regardless of the excision of a transposon. In the example provided this selectable marker is kanamycin resistance.

The progeny of the transformants are then screened for variegation on streptomycin. The most highly variegated progeny are likely to be homozygous for the introduced gene (see later). The homozygous state can be confirmed by test-crossing. Homozygous SPT::Ac containing plants should be used in crosses to individuals recessive for a targeted gene and their progeny are inspected for first streptomycin resistance and then the phenotype of interest.

Streptomycin resistance is preferred because it allows for non-lethal differentiation between sensitive and resistant plant cells. This is particularly important when only a small fraction of cells is expressing the novel phenotype as is the case upon transposon movement. Specifically, the progeny of the transformed plants are grown on streptomycin media, preferably containing approximately 1% glucose, 200 µg/ml -2000 µg/ml streptomycin (different plants may require different optimal concentrations) and MS salts (Murashige and Skoog, Physiol. Plant, 15 473-497, 1962). Specific optimal concentrations may be determined in known ways. Selection is made for plants which are streptomycin resistant.

Individuals showing an excision (i.e., streptomycin resistance) are next examined to determine which of these display loss of the phenotype associated with the gene of interest as the result of disruption of the gene by the transposon.

The altered plant is selected and the disrupted gene is identified and isolated, using known techniques, based on the presence of the transposon. Preferably, the identification and isolation are carried out by fragmenting the plant genome to create a library and searching the library with a probe containing DNA corresponding to some or all of the transposon DNA. The probe is used to obtain the disrupted gene containing the transposon, and the transposon DNA is then removed from the disrupted gene using known techniques. This linked DNA can then be used as a probe to isolate the undisrupted gene from a library of DNA made from plants carrying the undisrupted gene.

In a preferred embodiment, the method of the invention involves use of a construct (chimeric gene) comprising the 2' promoter from A. tumefaciens (for example, as developed by Velten et al., EMBO J 3 2723-2730, 1984) the streptomycin phosphotransferase coding sequence from Tn5 (Mazodier, et al., Nucleic Acids Res., 13, 195-203, 1985) and the Ac transposon (e.g., as described by Muller-Neumann, et al., Mol. Gen. Genet. 198:19-24, 1984).

In a preferred embodiment, the SPT expression cassette comprises a mutant allele of the Tn5 streptomycin resistance which is functional in E. coli and which contains a 2 amino acid deletion near the carboxy terminus (derived from plasmid pl16* as described by Mazodier et al., Mol. Gen. Genet., 204, 404-409(1986)). The cassette preferably also contains 3' polyadenylation signals derived from the octopine synthase gene of A. tumefaciens.

The SPT gene is preferably designed to include a unique restriction enzyme site, preferably in the 5= untranslated region of the gene This unique restriction site can be used to receive DNA carrying the Ac transposable element. It is preferred that the DNA surrounding the element, which also goes into this site, not contain a translational start signal (ATG). The fragment carrying the Ac element is then cloned into this site.

A preferred Agrobacterium binary vector plasmid (Van den Elzen et al., Plant Mol. Biol., 5:149–154, 1985) also contains a linked drug resistance gene, i.e., kanamycin resistance, to select for transformed plant cells. This transformation vector can be used to generate kanamycin resistant plants for screening of transformed plants.

Transformed plants are selfed and the progeny plated on media containing streptomycin. Those plants having the Ac excised from the SPT gene prior to fertilization exhibit a full green phenotype as compared to those having no excision which display a white phenotype and individuals having excision of the Ac at later stages of development display a green/white variegated phenotype.

Further crosses to detect the insertion of the Ac into the gene of interest are then made.

A preferred form of the construct is present in plasmid pJJ2853 within E. coli strain JM83. The construct has been deposited on Oct. 11, 1990 with the U.S.D.A. Agricultural Research Service, Patent Culture Collection, at 1815 N. University St., Peoria, Ill. 61604 and given an accession number NRRl B-18729. The construct can be isolated from the deposit by streaking out bacteria on tetracycline-containing media.

DEFINITIONS

"Gene of interest" refers to the gene being isolated.

"Transposon, transposable element or TE" all refer to a sequence of DNA which has the ability to move or "jump" to new locations in a genome.

"Construct" refers to a recombinant DNA which may be a cosmid, plasmid, or any nucleic acid comprising a vector able to incorporate into a host genome.

"Plant" includes a plant cell, a plant seed, and a part of a plant.

"Selectable" includes screenable.

EXAMPLES

The following examples are provided for illustration and are not to be construed as a limitation upon the claims.

A. Preparation of SPT Constructs, pJJ1571 and pJJ1601.

Figure 1:
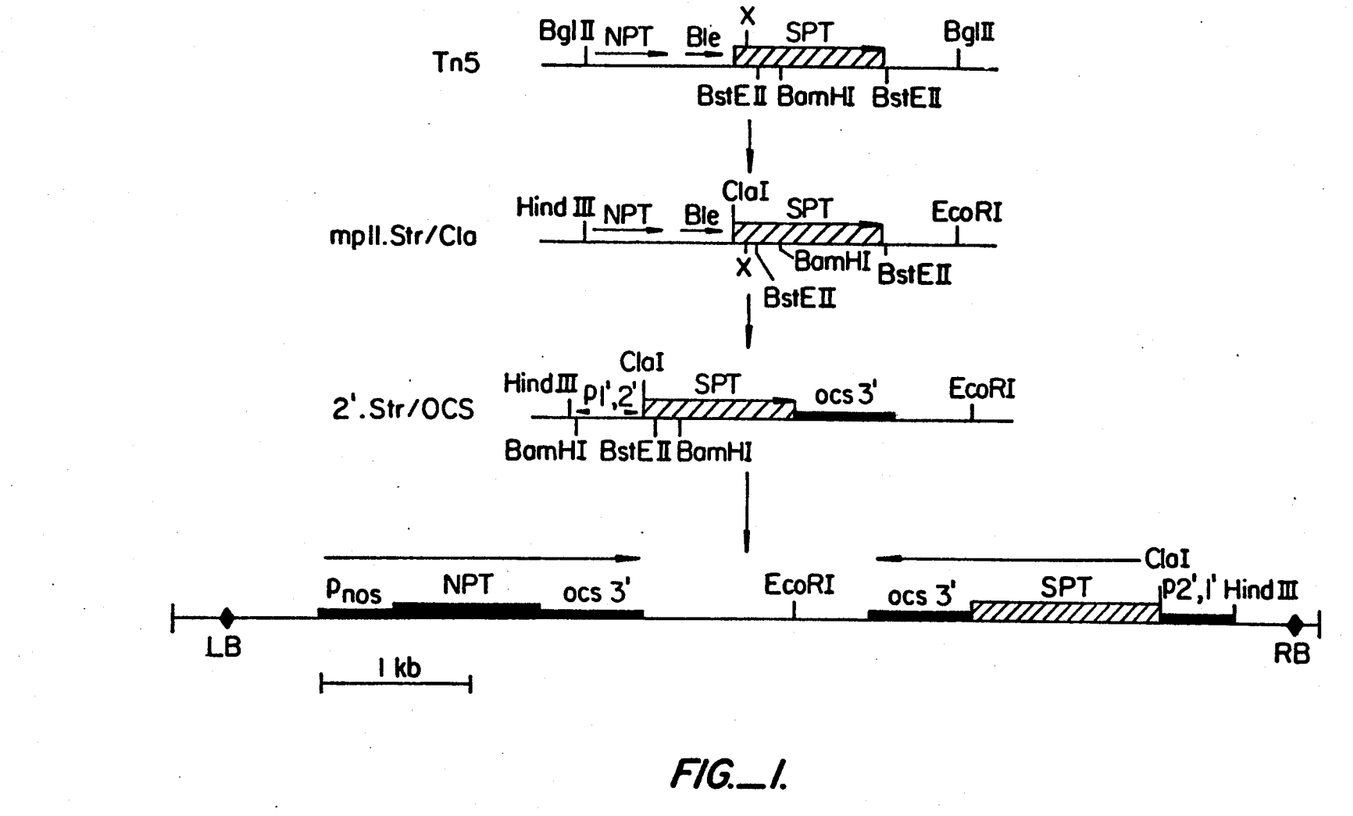
FIG. 1 is a construction of the chimeric SPT gene and cloning into the pAGS127 transformation vector. LB and RB indicate the left and right borders of the T-DNA. Note that pAGS127 carries an engineered NPT gene that confers kanamycin resistance in plants. The 2'.Str/ocs is in plasmid pJJ1571. pJJ1601 is the binary plasmid carrying linked chimeric SPT and NPT genes.
Figure 2:
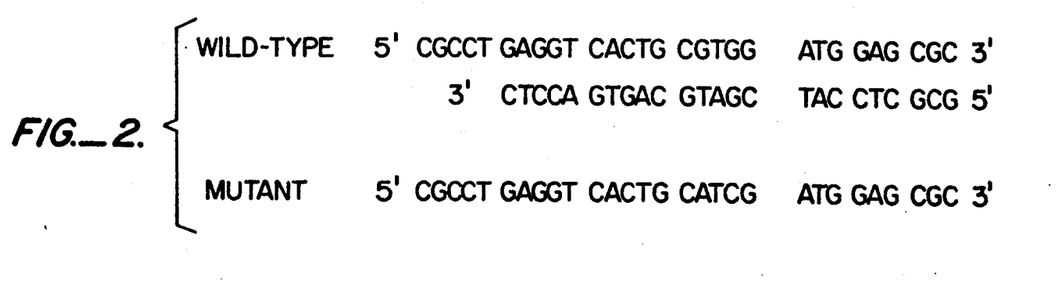
FIG. 2 is a wild-type and mutant SPT sequence around the translational initiation codon ATG. The nucleotides that have been changed are underlined. The mutagenic oligonucleotide is represented below the wild-type sequence.

Plasmid pJJ1571 contains a chimeric gene of 20 SPT. This plasmid has been previously described (Mol. Gen. Genet. 210:86-91, 1987). The construction of this DNA starting material is illustrated in FIG. 1. An internal BglII fragment containing the SPT coding sequence was excised from a clone carrying Tn5 (Nuc. Acid Res 13:195-203, 1985) and cloned into the M13 vector mpll. Single-stranded DNA was prepared from phage by standard techniques. An orientation was chosen such that the oligonucleotide sequence whose sequence is displayed in FIG. 2 would anneal and could be used for site-specific mutagenesis according to the gapped duplex DNA approach of Kramer et al. (Nucl. Acid Res. 12:9441-9456, 1984). Minipreps were performed to isolate the resulting replicative form phage DNAs which were then digested with ClaI and EcoRI to obtain mpll.Str/Cla.

The construction of 2'.Str/Ocs was accomplished using a three-way ligation involving: (i) pOP443 DNA (Velten et al. EMBO J. 3:2723-2730, 1984) cut with ClaI and EcoRI (ii) a ClaI/BamHI fragment derived from mpll.Str/Cla carrying the mutated 5' end of the SPT gene and (iii) a BamHI/EcoRI fragment carrying the C-terminal region of the SPT protein and the OCS polyadenylation site. This BamHI/EcoRI fragment had been cloned into pUC8 out of mpll.str/cla. Octopine synthase polyadenylation signals were provided by a 720bp PvuII fragment which had been cloned into a BstEII site (flush-ended using Klenow polymerase fragment and dNTPs) that lies 14 bp 3' to the SPT TAA termination codon in Tn5 DNA. The resultant plasmid pJJ1571 is maintained in E. coli.

The resulting 2'.Str/Ocs construction from pJJ1571 was digested with HindIII and EcoRI. The fragment encoding the production of SPT was ligated to DNA from a similarly digested binary vector, pAGS127, to obtain plasmid pJJ1601. This plasmid was mobilized into Agrobacterium LBA4404 using the mobilizing plasmid pRK2013 (Figurski and Helinski PNAS USA 76:1648-1652, 1979) and selecting for transconjugants by tetracycline resistance (1 $\mu$g/ml) on rifampicin (100 $\mu$g/ml) LB plates.

In order to maximize the level of streptomycin resistance, the mutant allele of the SPT gene which conferred streptomycin resistance on E. coli was used. DNA carrying this mutant allele was made available by P. Mazodier in the form of a plasmid pPM116*. Mol. Gen. Genet. 204:404-409 (1986). A region of the DNA carrying The mutation from ppm116* was cut out using the enzymes XhoI and NcoI and placed in the corresponding region of pJJ1571 which is occupied by wild type SPT DNA. Thus, by replacement, using known techniques, we placed the mutant form of the SPT gene downstream of the 2' promoter and upstream of the octopine synthase polyadenylation sites.

The resulting plasmid (pJJ2111) was used to generate a binary vector plasmid analogous to pJJ1601 by ligating pAGS127 DNA (cut with EcoRI and HindIII) to a fragment carrying the 2'/SPT fusion DNA derived from a EcoRI / HindIII digestion of pJJ2111. When this binary vector plasmid, pJJ2161, was mobilized into Agrobacterium LBA4404 as described above, and this strain used to transform plant protoplasts, an approximately equal frequency of kanamycin resistant and streptomycin resistant calli were observed (see Table 1).

To prepare the data for Table I, tobacco protoplasts were prepared and co-cultivated with LBA4404 Agrobacteria containing either pJJ1601, pJJ2161 or pJJ2668 (described below) for three days using standard techniques.

Protoplast isolation and cocultivation were carried out according to Van den Elzen, P., et al., Plant. Mol. Biol., 5:149-154 (1985). Selection for antibiotic resistance was carried out as follows. Protoplast derived calli were selected for resistance to streptomycin in RMO medium (Maliga, P., et al., Nature New Biol., 244:29-30, 1973) with 0.1 M mannitol, 1% sucrose and 500 $\mu$g/ml streptomycin sulphate. Kanamycin selection was carried out in RMO medium containing 3% sucrose and 50 $\mu$g/ml kanamycin sulphate.

B. Construction of SPT/Ac Construct - pJJ2853

In order to use the above-described chimeric SPT gene for Nicotiana tabacum cell transformation to assay transposon activity, a plasmid was prepared with a unique restriction site in the 5' leader of the SPT gene. There is a unique ClaI site in the SPT leader sequence, present as a result of the oligonucleotide mutagenesis. However, pJJ2161 contains another ClaI site which lies between the left border and the kanamycin resistance gene. A new binary plasmid was therefore constructed that contained only the ClaI site of the SPT leader.

This was carried out using binary vector plasmid pJJ1881, which is very similar to pAGSl12 (Van den Elzen et al., Plant Mol. Biol., 5:149-154, 1985) except that (i) it was made using the broad host range plasmid pRK290 (Ditta, G., et al., Proc. Nat'l. Acad. Sci. USA, 77:7347-7351, 1980) instead of pLAFR1 (Friedman, A.H., et al., Gene, 18:289-296, 1982) and (ii) it contains no EcoRI or HindIII sites. In Van den Elzen, P., et al., Plant Mol. Biol., 5:149-154, (1985), pAGS112 was made from pAGSlll and pLAFR1 by ligation of EcoRI cut fragments of each plasmid. Construction of pJJ1881 involved ligation of pRK290 DNA which had been digested with EcoRI and filled in with Klenow fragment polymerase and deoxynucleotide triphosphates (dNTPs) to the T-DNA- carrying fragment of pAGSlll produced by digestion with EcoRI and HindIII and filling in with Klenow polymerase and dNTPs. These fragments were joined by blunt end ligation, and the clone of the resulting ligation product, pJJ1881, accordingly had no EcoRI or HindIII sites, and no cos site (required for a plasmid to be a cosmid), but otherwise corresponded to pAGS112.

The ClaI site in pJJ1881 was removed by digesting with ClaI, treating with Klenow enzyme and deoxynucleoside triphosphates and then recircularizing with DNA ligase. The plasmid pJJ1912, unlike pAGS127, could not be cut with EcoRI and HIndIII to receive the 2'/SPT DNA. Instead, it was digested with HpaI to linearize at a unique HpaI site near the right border sequences. This cut DNA was ligated to 2'/SPT DNA which had been excised from pJJ2111 by digestion with SmaI and FspI. The SmaI site of pJJ2111 is derived from the mpll polylinker and lies immediately adjacent to the EcoRI site illustrated in FIG. 1 at line 3 (2'.Str/.OCS). An FspI site (TGCGCA) lies in the 1'2' promoter at position 368 in the sequence of this region presented by Velten, et al., EMBO J 3:2723-2730, (1984). The 1' promoter, described in Velten et al., EMBO J., 3:2723-2730 (1984) is divergently transcribed from the 2' promoter. pJJ2111 was digested with FspI and SmaI and the appropriate fragment of about 2.4 kb was gel purified prior to ligation to HpaI digested pJJ1912 DNA. This ligation gave rise to a plasmid which contained chimeric SPT and NPT genes with a unique ClaI site in the SPT gene. The orientation of the SPT gene was such that the SPT gene and the NPT genes are transcribed in from the right and left borders respectively. This plasmid, pJJ2668 (depicted in FIG. 3), could then be linearized with ClaI and ligated to DNA carrying the Ac transposon.

The Ac transposon which was used is a chimeric Ac with one end derived from a bronze isolate of Ac (Dooner et al., Mol. Gen. Genet., 200:240-246, 1985) and the other end isolated from waxy m-7 (Behrens et al., Mol. Gen. Genet., 194:346-347, 1984). Furthermore, this Ac allele has been mutagenized in such a way that it contains the restriction site BglII in a position which will not interrupt important sequences for Ac transposition. As an optional step, this BglII site was filled in with Klenow polymerase and dNTPs to create a ClaI site.

Figure 3:
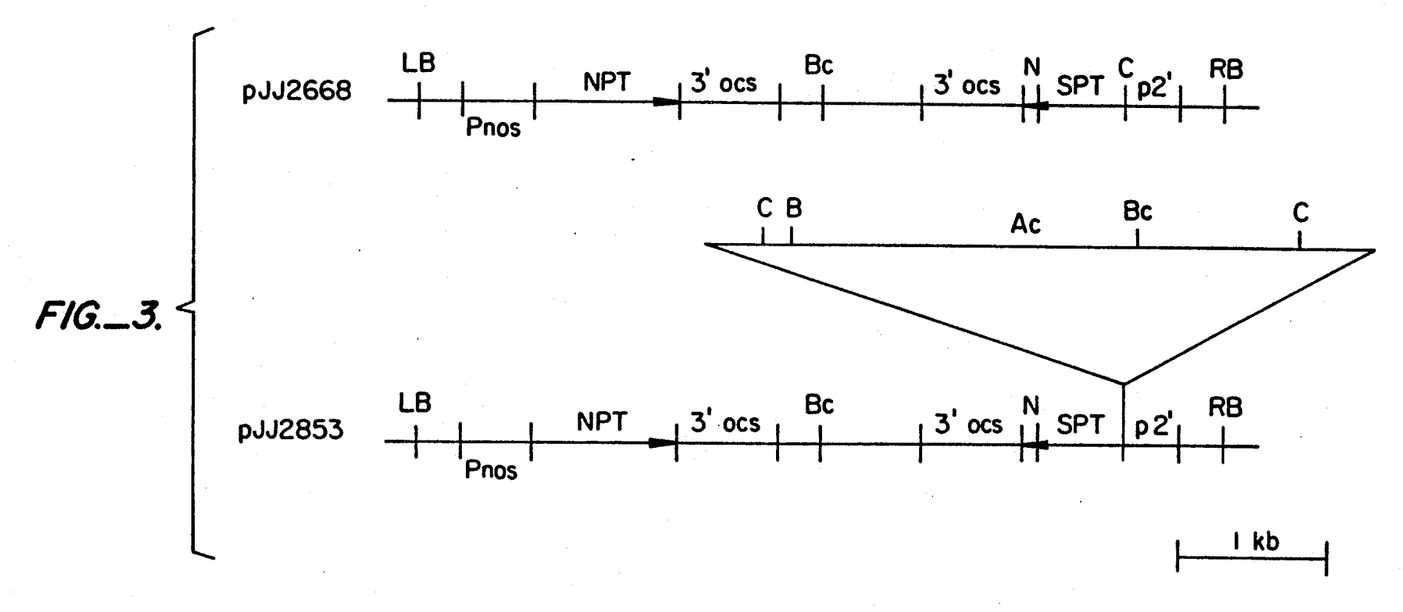
FIG. 3 is a schematic representation of plasmids pJJ2668 and pJJ2853. LB and RB represent the left and right borders of the T-DNA. B, C, Bc and N represent endonuclease restriction sites: BamHI, ClaI, BclI and NcoI, respectively.

A clone was generated, pJJ2542, which carries 18 bp of waxy m-7 DNA between Ac sequences and the restriction site SstI at one end, and 47 bp of bronze flanking DNA between an StuI site and the other end of Ac. Thus digestion with StuI and SstI will cut Ac and minimal flanking sequences away from the plasmid vector. This flanking DNA does not contain any ATG codons. The Ac-carrying plasmid was digested with SstI and StuI and the SstI ends were rendered flush ended using T4 polymerase and dNTPs. Plasmid pJJ2668 was digested with ClaI and this DNA was also rendered flush ended using Klenow polymerase and dNTPs. The fragments were ligated together and a plasmid pJJ2853 was obtained which carried the Ac transposon in the leader of the 2'/SPT gene in such a way that excision of Ac was likely to reconstitute streptomycin resistance. Maps of the T-DNA (transferred DNA) of pJJ2668 and pJJ2853 are shown in FIG. 3.

C. Use of the SPT/Ac Construct to Reveal Ac Transposition in Tobacco.

The plasmid pJJ2853 was mobilized into A. tumefaciens LBA4404 and the resulting strain was used in leaf disc transformation experiments (Horsch et al., Science, 227:1229, 1985) of tobacco cv. Petite Havana. Transformed shoots were selected for kanamycin resistance. Shoots were rooted and transferred to the greenhouse, the plants were allowed to flower, and seed were collected from selfed or test crossed flowers.

Seed from independent transformants were plated on streptomycin (200 µg/ml) medium or on kanamycin (200 µg/ml) medium. The seedlings grown upon the streptomycin medium demonstrated an array of different variegated phenotypes. Some seedlings exhibited intense variegation, with many green spots per seedling while others exhibited one or very few spots per seedling. In some individuals relatively large green sectors were observed. Several individuals were observed in which a sector extended from one cotyledon to another. Fully green individuals were observed with a consistent frequency in each batch of seed.

Table II shows a genetic analysis of kanamycin resistance and streptomycin resistance and variegation for two transformants, 2853.2 and 2853.6. The kanamycin resistance segregation demonstrates the existence of two kanamycin resistant (KANR) loci in 2853.2 and one KANR locus in 2853.6. Seedlings which germinated on streptomycin were classified by number of green spots per seedling. Back cross progeny of 2853.2 and 2853.6 showed an approximately 1:1 ratio of individuals with no spots to individuals with 1-6 spots. This is consistent with the presence in each transformant of one locus that confers the capacity to exhibit variegation on streptomycin.

In selfed progeny, approximately ¼ (2853.2) or ¼ (2853.6) showed no variegation. Some selfed progeny were observed with more variegation than could be seen in any backcross progeny. This would be consistent with th idea that homozygotes usually exhibit more variegation than heterozygotes. Such an interpretation suggests that Ac in tobacco does not exhibit the negative effect of increased Ac dosage on transposition frequency genetically (see later).

D. Southern Blot Analysis of Progeny Which Are Fully Green on Streptomycin.

Tests were performed to establish not only that green sectors are associated with Ac excision but also that such excision events are associated with reinsertion of the Ac element elsewhere. DNA was isolated from plants derived from seedlings which were fully green on streptomycin, and blot hybridizations were conducted. Genomic DNA was digested with NcoI (which does not cut in Ac but does cut in the SPT gene) and blots were hybridized with an Ac homologous probe.

Blot hybridizations were conducted using genomic DNA from untransformed tobacco; from the primary transformant 2853.2 and from 4 progeny of the self-mating which were fully green on streptomycin; and from the primary transformant 2853.6 and from 5 different streptomycin resistant individuals from the respective self-mating. Transformant 2853.2, which showed two independently segregating KANR loci, showed 2 Ac homologous bands of 5.3 kb and 7.6 kb. Transformant 2853.6, which showed one KANR locus, contained one Ac homologous band of about 13.0 kb. Two of the four streptomycin resistant progeny of transformant 2853.2 showed new Ac-homologous bands. All of the five streptomycin resistant progeny of 2853.6 exhibited the same new Ac-homologous 8.5 kb band, while two of them also exhibited an additional new band of about 8.7 kb. There are no NcoI sites in pJJ2853 between the site in the SPT gene and the right border (about 6.5 kb). The size of the Ac-homologous band in 2853.6 (13.0 kb) is consistent with T-DNA insert which consists of a two-copy inverted repeat about the right border. The 8.5 kb Ac-homologous band common to all 2863.6 STRR plants (8.5 kb) was due to excision of an Ac from one copy of this inverted repeat leaving an Ac-homologous NcoI fragment which is 4.6 kb smaller. Thus, in this genetic stock, an Ac probe visualizes not only the empty site but also the new Ac location, if any.

Overall, all five of the 2853.6 streptomycin resistant progeny showed Ac excision, and two of them showed a new Ac band. These data demonstrate that selection for streptomycin resistance selects for Ac excision events. That is, these data are consistent with the conclusion that these seedlings are green on streptomycin due to excision of Ac from the SPT::Ac gene. Furthermore, a substantial fraction (about one half) of individuals which exhibited germinal excision of Ac from an SPT::Ac gene showed evidence (new Ac-homologous bands) for reinsertion of Ac at new locations in the genome.

E. Genetic Tests of Altered Dosage Effect of Ac in Tobacco.

If the highly variegated individuals in progeny from the self-mating are homozygotes for the introduced SPT::Ac allele, one would expect that both selfed and backcrossed progeny of these second generation transformed plants would be 100% kanamycin resistant. Furthermore, one would expect that selfed progeny would be 100% highly variegated, and that backcrossed progeny would be 100% light variegated.

To test these predictions, highly variegated (HV) 2853.6 progeny were transferred to media lacking streptomycin and then, once fully green leaves appeared, were grown to full size and selfed and backcrossed. Progeny seed were plated on kanamycin and streptomycin. Of twelve HV individuals, eleven showed 100% kanaymcin resistance in their progeny. More importantly, (Table III) when test cross or selfed progeny seed from three different homozygous HV individuals (HV10, HV11 and HV12) were plated on streptomycin, nearly 100% of selfed progeny showed 7 or more spots per seedling while about 90% of the backcrossed progeny showed 1-6 spots per seedling. These data lead to the inference that Ac in tobacco is not subject to the negative effect of dosage on transposition frequency which is observed in corn.

F. Isolation of Gene for Tobacco Mosaic Virus Resistance in Tobacco Using SPT::Ac 2853.

The gene for tobacco mosaic virus (TMV) resistance is isolated from tobacco as set forth below. This gene (the N gene) will be referred to as the gene of interest.

(1) Multiple transformants of TMV resistant tobacco (target plant) are made with SPT::Ac 2853 (produced in accordance with the method of Example B above) in accordance with the method of Example C above.

(2) Linkage between the introduced DNA of different transformants and the resistant allele of the gene of interest is mapped by crossing two generations to TMV sensitive lines and looking for linkage between kanamycin resistance and TMV resistance.

(3) A transformant is selected in which the SPT::Ac construct is linked to (and preferably within 10 map units of) the gene of interest and a homozygote is obtained from selfed progeny of this transformant.

(4) Multiple crosses are carried out between the SPT::Ac homozygote and individuals homozygous for the disease sensitive gene of interest.

(5) Seed from the crosses of Step 4 are plated out on streptomycin plates under the conditions of Example C above and selection is made for individuals in which excision is shown to have taken place (as detected by the appearance of fully green seedlings).

(6) Streptomycin resistant plants are tested for sensitivity to TMV. To avoid killing the desired genotype, cuttings are derived from streptomycin resistant lines and these cuttings are tested for disease sensitivity.

(7) The Ac-mutagenized gene of interest is isolated from a plant sensitive to TMV using hybridization techniques, with Ac as a probe, in order to isolate plant DNA carrying Ac.

(8) The plant DNA that flanks Ac is used as a probe to a DNA library from a resistant plant to isolate the unmutagenized resistance gene.

The advantage of this procedure is that if one is looking for individuals in which the gene of interest has been disrupted by transposon insertion, it is far more economical if one can use a reliable method to prescreen so that one only inspects individuals in which transposition is known to have taken place.

TABLE I

Tranformation of Tobacco Protoplasts for Resistance to Streptomycin and Kanamycin.

| VECTOR | SPT[a] | PROM. | SELECT[b] | NO. OF COLONIES | RESISTANT | % |
|---|---|---|---|---|---|---|
| | | | Sm | $1.1 \times 10^4$ | 0 | 0 |
| | | | Km | $1.1 \times 10^4$ | 0 | 0 |
| pJJ1601 | wt | 2'1' | Sm | $3.6 \times 10^4$ | 0 | 0 |
| | | | Km | $3.6 \times 10^4$ | 71 | 0.2 |
| pJJ2161 | 116* | 2'1' | Sm | $2.4 \times 10^4$ | 2020 | 8.3 |
| | | | Km | $9.7 \times 10^3$ | 600 | 6.2 |
| pJJ2668 | 116* | 2' | Sm | $2.1 \times 10^4$ | 733 | 3.6 |
| | | | Km | $9.8 \times 10^3$ | 260 | 2.7 |

[a]The mutant SPT derived from plasmid pPM116* (Molec. Gen. Genet. 204:404–409, 1986).
[b]Selection was carried out in the presence of 50 μg/ml kanamycin sulphate or 500 μg/ml streptomycin sulphate in RMO medium.

TABLE II

GENETIC ANALYSIS OF KAN AND STR::AC SEGREGATION IN TRANSFORMED PLANTS 2853.2, 2853.6

| CROSS | KANAMYCIN RESISTANCE SEGREGATION | | | | |
|---|---|---|---|---|---|
| | KANR | KANS | TOTAL | RATIO | chi[2] |
| 2853.2 | 169 | 71 | 240 | 1:1 | 40.0 |
| TEST (M) | | | | 3:1 | 2.68 |
| 2853.2 | 142 | 53 | 195 | 1:1 | 40.6 |
| TEST (F) | | | | 3:1 | 0.49 |
| 2853.6 | 170 | 178 | 348 | 1:1 | 0.18 |
| TEST (M) | | | | 3:1 | 126 |
| 2853.6 | 58 | 65 | 123 | 1:1 | 0.40 |
| TEST (F) | | | | 3:1 | 50.8 |

| CROSS | SEGREGATION FOR GREEN-WHITE VARIEGATION # OF SPOTS PER SEEDLING | | | | | | | |
|---|---|---|---|---|---|---|---|---|
| | 0 | 1-3 | 4-6 | 7-9 | 10-15 | 16+ | GREEN | TOTAL |
| 2853.6 SELF | 212 | 267 | 48 | 88 | 16 | — | 6 | 634 |
| 2853.6 TEST (M) | 57 | 47 | 12 | — | — | — | — | 116 |
| 2853.6 TEST (F) | 46 | 43 | 4 | — | — | — | 1 | 93 |
| 2853.2 SELF | 50 | 68 | 11 | 8 | 28 | 27 | 1 | 193 |
| 2853.2 TEST (M) | 41 | 38 | — | — | — | — | — | 79 |

TABLE II-continued

GENETIC ANALYSIS OF KAN AND STR::AC SEGREGATION IN TRANSFORMED PLANTS 2853.2, 2853.6

| | | | | | | | | |
|---|---|---|---|---|---|---|---|---|
| 2853.2 TEST (F) | 82 | 54 | 5 | — | 1 | — | — | 141 |

M = Ac parent as male, F = Ac parent as female

TABLE III

GREEN/WHITE VARIEGATION ON STREPTOMYCIN IN SELF-POLLINATED AND TEST-CROSSED PROGENIES OF HOMOZYGOUS SPT::Ac PLANTS

| | # OF SPOTS PER SEEDLING | | | | | | | |
|---|---|---|---|---|---|---|---|---|
| | 0 | 1-3 | 4-6 | 7-9 | 10-15 | 16+ | TOTAL | FULL | GREEN |
| HV10 SELF | 0 | 0 | 0 | 8 | 46 | 54 | 108 | 22/570 | (3.9%) |
| HV10 TEST | 0 | 49 | 45 | 3 | 3 | 0 | 100 | 26/744 | (3.5%) |
| HV11 SELF | 0 | 0 | 0 | 8 | 46 | 48 | 102 | 6/240 | (2.5%) |
| HV11 TEST | 1 | 56 | 41 | 4 | 5 | 0 | 107 | 5/420 | (1.2%) |
| HV12 SELF | 0 | 1 | 0 | 3 | 47 | 50 | 101 | 21/730 | (2.9%) |
| HV12 TEST | 0 | 50 | 51 | 4 | 4 | 0 | 109 | 7/548 | (1.2%) |

What is claimed is:

1. A method for isolating a plant gene of interest conferring a characteristic phenotype, wherein said method comprises: (a) transforming a plant carrying the gene of interest to make transformed plants by introduction of a DNA construct containing an AC transposon inserted within a selectable marker effecting resistance to streptomycin wherein the transposon renders the marker inoperable; and (b) isolating those transformed plants having the transposon excised from the marker and inserted into the plant gene of interest.

2. The method of claim 1 wherein the selectable marker is derived from the gene encoding streptomycin phosphotransferase.

3. The method of claim 2 wherein the selectable marker is derived from the gene encoding streptomycin phosphotransferase contained in the bacterial transposon Tn5.

4. The method of claim 3 wherein the streptomycin phosphotransferase is operably linked to a promoter selected from the group consisting of the 2' promoter from *Agrobacterium tumefaciens* and the 35s promoter from cauliflower mosaic virus.

5. The method of claim 1 wherein transformation is achieved using *Agrobacterium tumefaciens*.

6. The method of claim 1 wherein the plant cell is a dicot.

7. The method of claim 11 wherein the dicot is a species of Nicotiana.

8. The method of claim 1 wherein the plant gene regulates resistance to disease.

9. The method of claim 1 which comprises recombining the AC transposon into the selectable marker rendering the marker inoperable; transforming a plant cell with another marker linked to the inoperable marker; maintaining the transformed cells under conditions suitable for the transposon to transpose from the marker to the plant gene; and isolating those cells having the transposon recombined into the plant gene.

10. The method of claim 9, said method comprising the steps of:

(a) selecting a plant containing the plant gene of interest;

(b) preparing a DNA construct comprising a plant promoter operably fused to a DNA segment coding for streptomycin phosphotransferase and further comprising the transposon Ac wherein the transposon is positioned within the DNA segment so as to render the streptomycin phosphotransferase gene incapable of conferring resistance to streptomycin in the plant hosting the construct;

(c) introducing said DNA construct into the plant by transformation to yield a multiplicity of transformed plants and identifying plants in which said introduced DNA construct is genetically linked to the target gene;

(d) growing the transformed plants in the presence of streptomycin and selecting from the plants a set of plants which exhibit excision in which the Ac DNA has excised from the streptomycin phosphotransferase gene, said plants which exhibit excision being identifiable by streptomycin resistance;

(e) selecting from the plants which exhibit excision, a plant in which the desired phenotype is altered as the result of transposition of the Ac DNA into the plant gene encoding the desired phenotype;

(f) creating a genomic library from the DNA of the plant of step e; and (g) isolating from said genomic library a clone containing transposon Ac DNA using labeled transposon Ac DNA as a probe; and (h) isolating the gene of interest from a library derived from a plant containing the gene of interest by using as a probe DNA linked to transposon Ac in said clone containing transposon Ac DNA.

11. A DNA construct comprising a DNA segment containing a selectable marker for use in plant cells, said marker effecting resistance to stroptomycin wherein the marker is operably linked to a plant promoter and further comprising an AC transposon positioned within the segment, said transposon rendering the marker inoperable.

12. The construct of claim 11 wherein the gene encodes for streptomycin phosphotransferase.

13. The construct of claim 11 wherein the construct further comprises a second selectable marker operable in a plant cell.

14. The construct of claim 13 wherein the second selectable marker encodes for resistance to kanamycin.

15. The construct of claim 14 capable of being stably maintained by *Agrobacterium tumefaciens*.

16. A host cell containing a DNA construct comprising a DNA segment comprising a selectable marker effecting resistance to streptomycin, said marker for use in plant cells wherein the marker is operably linked to a plant promoter and comprises an AC transposon positioned within the segment rendering the marker inoperable.

17. The cell of claim 16 being further described as an *E. coli* bacterium containing pJJ2853 as deposited with the Patent Culture Collection of the United States Department of Agriculture and having accession number NRRL B-18729.